United States Patent [19]

Maurer

[11] 4,049,526
[45] Sept. 20, 1977

[54] EXTENDED-LIFE ELECTRODE

[75] Inventor: James I. Maurer, St. Clair Shores, Mich.

[73] Assignee: Oxy Metal Industries Corporation, Warren, Mich.

[21] Appl. No.: 723,821

[22] Filed: Sept. 16, 1976

[51] Int. Cl.$^2$ ............................................. G01N 27/30
[52] U.S. Cl. ................................................ 204/195 M
[58] Field of Search ........................... 204/1 B, 195 M

[56] References Cited
U.S. PATENT DOCUMENTS

| 3,431,182 | 3/1969 | Frant | 204/1 T |
| 3,607,710 | 9/1971 | Farren et al. | 204/195 M |

Primary Examiner—G. L. Kaplan
Attorney, Agent, or Firm—Arthur E. Kluegel; Richard P. Mueller; Bertram F. Claeboe

[57] ABSTRACT

Disclosed is an electrode design which exhibits extended service live when immersed in aqueous fluoride ion containing compositions. The electrode comprises a fluoride ion sensitive membrane adhered to an insulating electrode shell by means of a slow-setting cement. At least one deposit of a cyanoacrylate glue adheres to the membrane and the electrode shell so as to prevent contact between the aqueous composition and the slow-setting cement.

2 Claims, 1 Drawing Figure

EXTENDED-LIFE ELECTRODE

BACKGROUND OF THE INVENTION

This invention relates to the art of electrode manufacture. More specifically, it relates to the art of manufacturing fluoride sensitive electrodes employing a fluoride sensitive membrane or crystal.

Numerous electrodes have been developed in the art which are capable of ion selectivity. U.S. Pat. No. 3,431,182 discloses an electrode suitable for measuring fluoride ion activity in an aqueous solution. The electrode of the patent employs a fluoride ion sensitive membrane of a solid ionic fluoride compound which membrane is substantially insoluble in the aqueous fluoride composition. The membrane is contacted at one surface by the aqueous composition and at the other surface by a reference electrolyte providing a fixed contact potential. Exemplary membranes are formed of fluorides of the lanthanide series of selected rare earth metals.

While the electrode design of the above patent is effective to measure the fluoride ion activity in a process solution, it has been found that the service life of such electrodes is highly unsatisfactory. Most of such electrodes have a service life of less than 6 months and, in some cases, as short as 2-3 weeks. The problem which has been experienced is a loss of seal between the sensing membrane and the plastic body of the electrode shell. The show-setting cement employed to adhere the membrane to the shell begins to crack and permits the process fluid to enter the internals of the electrode. Epoxy cements are normally employed to secure the membrane to the shell. Epoxy cements generally exhibit resistance to chemicals and are capable of withstanding modest temperature variations; however, the epoxy cement is apparently unsuitable for this particular application in measuring the fluoride content of the process solutions.

SUMMARY OF THE INVENTION

It has now been discovered that if the slow-setting cement employed to adhere the sensing membrane to the electrode shell is isolated from the process solution by means of a cyanoacrylate glue, the service life of a fluoride electrode may be greatly extended.

DETAILED DESCRIPTION OF THE INVENTION

Figure 1:
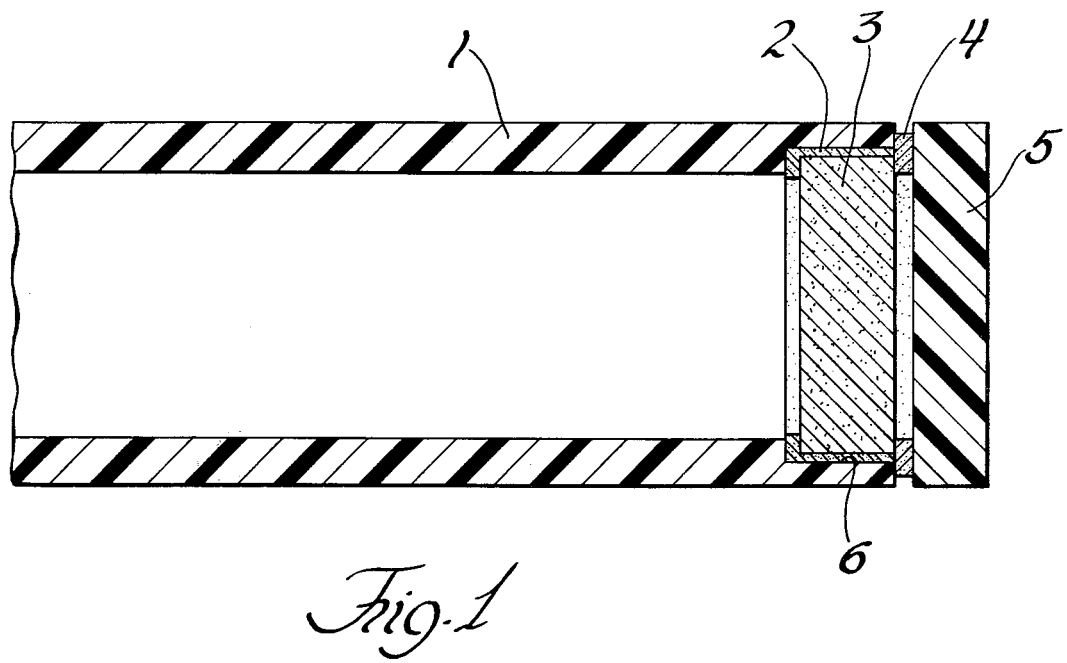
FIG. 1 is a longitudinal section of an electrode manufactured in accordance with the present invention.

FIG. 1 depicts one embodiment of the electrode of the present invention. The figure omits all reference solutions, the reference electrode, and the electrical connections. Electrode shell 1 provided with aperture 6 is tubular in shape and may be constructed of any non-conductive insulating material. Preferably, the material of manufacture is a sturdy, rigid, non-porous plastic which is chemically resistant to the processing solution. The particular material of construction is not critical and may be, for example, an unplasticized polyvinylchloride, polytetrafluoroethylene, an epoxy resin or the like. Fluoride sensing membrane 3 is adhered to electrode shell 1 so as to cover aperture 6 by means of a layer of an epoxy cement 2. The epoxy cement 2 extends about the entire circumference of membrane 3. Accordingly, when the electrode is immersed in a process solution, the solution is prevented from entering the internal of electrode shell 1 by virtue of the presence of the epoxy cement about the parameter of the membrane 3. The electrode as represented by the shell 1, membrane 3, and epoxy cement 2 represents the current state of the art for fluoride electrodes. In accordance with FIG. 1, the electrode of the present invention additionally contains an insulating member 5 which is adhered to shell 1 and membrane 3 by means of a cyanoacrylate glue 4. In the drawing, the cyanoacrylate glue deposit and the insulating member are both annular in shape and sized so as to completely isolate the layer of epoxy cement from the process solution when the electrode is immersed.

A slow-setting cement such as the epoxy is preferred for use in bonding the sensing membrane to the electrode shell because it enables the manufacturer of the electrode some latitude in placing the membrane within the aperture of the electrode shell. While the cyanoacrylate glue appears much more resistant to the process solution, its quick setting properties (less than 10 seconds) make it undesirable for use in bonding the membrane to the electrode shell. Accordingly, epoxy cement is preferably employed for bonding the shell to the membrane and a cyanoacrylate glue is employed to isolate the epoxy cement from the process solution. The use of the additional insulating element 5 simplifies the isolation of the epoxy cement from the process solution and also provides additional mechanical strength to the electrode. Suitable materials of construction for electrode shell 1 and membrane 3 are set forth in U.S. Pat. No. 3,431,182 which is incorporated herein by reference. The materials suitable for the electrode shell may also be employed to construct the insulating member 5. The cyanoacrylate glue contains a cyanoacrylate ester. Such glue is available, for example, from Woodhill Chemical Sales Corporation under the trademark SUPER GLUE®3.

The configuration of the cyanoacrylate glue deposit on the electrode may be of any design which is effective to isolate the epoxy cement from the process solution. While a layer of the cyanoacrylate glue by itself may be employed to isolate the epoxy cement from the process solution, it is preferred to employ the insulating member in order to help protect the electrode from mechanical shock.

What is claimed is:

1. An extended-life electrode suitable for measuring the concentration of fluoride ion in an aqueous solution comprising an insulating electrode shell having an aperture therein, a fluoride sensitive membrane adapted to cover said aperture, a layer of slow-setting cement located between the membrane and the perimeter of the shell aperture and adherent to both the membrane and shell and means for isolating the slow-setting cement layer from the solution comprising a cyanoacrylate glue adhered to the membrane and the shell.

2. The electrode of claim 1 wherein the isolating means comprise an insulating member formed so as to have a surface capable of covering the entire slow-setting cement layer without entirely covering the membrane, said member being bonded to the shell and membrane by a deposit of a cyanoacrylate glue.

* * * * *